US007678552B2

(12) United States Patent
Kornblith

(10) Patent No.: US 7,678,552 B2
(45) **Date of Patent: *Mar. 16, 2010**

(54) METHOD FOR SELECTING THERAPEUTIC AGENTS FOR CANCER TREATMENT

(75) Inventor: Paul L. Kornblith, Pittsburgh, PA (US)

(73) Assignee: Precision Therapeutics, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/208,076

(22) Filed: Sep. 10, 2008

(65) Prior Publication Data

US 2009/0042225 A1 Feb. 12, 2009

Related U.S. Application Data

(63) Continuation of application No. 11/504,098, filed on Aug. 15, 2006, now Pat. No. 7,563,593, which is a continuation of application No. 11/073,931, filed on Mar. 8, 2005, now Pat. No. 7,112,415, which is a continuation of application No. 09/039,957, filed on Mar. 16, 1998, now Pat. No. 6,933,129, which is a continuation-in-part of application No. 08/679,056, filed on Jul. 12, 1996, now Pat. No. 5,728,541.

(51) Int. Cl.
*C12Q 1/24* (2006.01)

(52) U.S. Cl. ........................... 435/30; 435/29; 435/261

(58) Field of Classification Search .................. 435/30, 435/29, 261
See application file for complete search history.

(56) References Cited

U.S. PATENT DOCUMENTS

| | | | | |
|---|---|---|---|---|
| 5,728,541 | A * | 3/1998 | Kornblith | 435/29 |
| 6,887,680 | B2 * | 5/2005 | Kornblith | 435/29 |
| 6,933,129 | B1 * | 8/2005 | Kornblith | 435/29 |
| 7,112,415 | B2 * | 9/2006 | Kornblith | 435/29 |
| 7,314,731 | B2 * | 1/2008 | Kornblith | 435/29 |
| 7,501,260 | B2 * | 3/2009 | Kornblith | 435/29 |

OTHER PUBLICATIONS

Lipton, L. et al. Tissue Culture Studies on Human Pituitary Tumours. Acta Endocrinologica 88 239-249, 1978.*

Kornblith P. et al. Response Variability of Human Brain Tumors to AZQ in Tissue Culture. J of Neuro Oncology 4 49-54, 1986.*

PL Kornblith et al., "Response variability of human brain tumors to AZQ in tissue culture," Journal of Neuro-Onocology, 1986, pp. 49-54, vol. 4, Martinus Nijhoff Publishers, Boston.

RS Weinstein et al., "Ultrastructure of a cloned astrocytoma in tissue culture," Cancer, 1971, pp. 1174-1181, vol. 27.

PMcL Black et al., "Ultrastructural and electrophysiological features of meningioma whorls in tissue culture," Acta Neuropathol (Berl), 1979, vol. 46, pp. 33-38.

RM Scott et al., "Invasiveness in tissue culture: A technique for study of gliomas," Surg Forum, 1978, pp. 531-533, vol. 29.

T. Liszczak et al., "Morphological, biochemical, ultrastructural, tissue culture and clinical observations of typical and aggressive craniopharyngiomas," Acta Neuropathol (Berl), 1978, pp. 191-203, vol. 43.

PL Kornblith et al., "Growth-inhibitory effects of diphenylhydantoin on human brain tumor cells in culture," Neurosurgery, 1978, pp. 122-127, vol. 2.

RR Weichselbaum et al., "Characterization and radiobiologic parameters of medulloblastoma in vitro," Cancer, 1977, pp. 1087-1096, vol. 40.

RL Martuza et al., "Characteristics of human optic gliomas in tissue culture," J. Neurosurg, 1977, pp. 78-84, vol. 46.

MA Oberc-Greenwood, et al., "Ultrastructural features of the lymphocyte-stimulated halos produced by human glioma-derived cells in vitro," Journal of Neuro-Oncology, 1986, pp. 387-396, vol. 3.

BH Smith et al., "Membrane and cytoplasmic changes in 1,3-bis (2-chloroethy 1)- 1—nitrosourea (BCNU)-sensitive and resistant human malignant glioma-derived cell lines," Journal of Neuro-Oncology, 1983, pp. 237-248, vol. 1.

GA Curt et al., "Phase II and pharmacokinetic study of aziridinylbenzoquinone (2,5-diaziridinyl-3, 6-bis(carboethoxyamino)-1,4 benzoquinone, diaziquone, NSC 182986) in high grade gliomas," Cancer Research, 1983, pp. 6102-6105, vol. 43, Issue 12 pt 1.

N Shitara et al., "Flowcytometric and cytogenetic analysis of human cultured cell lines derived from high- and low-grade astrocytomas," Acta Neuropathol (Berl), 1983, pp. 40-48, vol. 60.

MK Gumerlock et al., "Chemical differentiation of cultured human glioma cells: Morphologic and immunologic effects," Surgical Forum, 1981, pp. 475-477, vol. XXXII.

PL Kornblith et al., "Growth-inhibitory effect of diphenylhydantoin on murine astrocytomas," Neurosurgery, 1979, pp. 259-263, vol. 5.

MC Trachtenberg et al., "Biophysical properties of cultured human glial cells," Brain Research, 1972, pp. 279-298, vol. 38.

(Continued)

*Primary Examiner*—Ralph Gitomer
(74) *Attorney, Agent, or Firm*—Cooley Godward Kronish LLP

(57) ABSTRACT

An improved system for screening a multiple of candidate therapeutic or chemotherapeutic agents for efficacy as to a specific patient, in which a tissue sample from the patient is harvested, cultured and separately exposed to a plurality of treatments and/or therapeutic agents for the purpose of objectively identifying. One particularly important tissue sample preparation technique is the initial preparation of cohesive multicellular particulates of the tissue sample. For assays concerning cancer treatment, a two-stage evaluation is contemplated in which both acute cytotoxic and longer term inhibitory effect of a given anti-cancer agent are investigated. The tissue sample technique of the present invention is also useful in assaying expression and/or secretion of various markers, factors or antigens present on or produced by the cultured cells for diagnostic purposes and for using such expression to monitor the applicability of certain candidate therapeutic or chemotherapeutic agents and the progress of treatment with those agents.

59 Claims, No Drawings

OTHER PUBLICATIONS

J. Lightbody et al., "Biochemically differentiated clonal human glial cells in tissue culture," J. Neurobiology, 1970, pp. 411-417, vol. 1, No. 4.

PMcL Black et al., "Biophysical properties of human astrocytic brain tumor cells in cell nature," Journal of Cellular Physiology, 1980, pp. 565-570, vol. 105.

TM Liszczak et al., "Ultrastructure of human endometrial epithelium in monolayer culture with and without steroid hormones," In Vitro, 1977, pp. 344-356, vol. 13, No. 6.

TM Liszczak et al., "Procedure for the embedment and ultrastructural visualization of cells cultured on plastic microtest plates," Journal of Immunological Methods, 1977, pp. 131-134, vol. 15.

RM Stewart et al., "Glutamate accumulation by human gliomas and meningiomas in tissue culture," Brain Research, 1976, pp. 441-452, vol. 118.

PL Kornblith et al., "The future of therapy for glioblastoma," Surg Neurol, 1993, pp. 538-543, vol. 39.

PL Kornblith, "Management of malignant gliomas," Neurosurgery Quarterly, 1991, pp. 97-110, vol. 1, Issue 2.

PL Kornblith et al., "Chemotherapy for malignant gliomas," Journal of Neurosurgery, 1988, pp. 1-17, vol. 68, Issue 1.

PE McKeever et al., "Products of cells cultured from gliomas: VI. Immunofluorescent, morphometric, and ultrastructural characterization of two different cell types growing from explants of human gliomas," American Journal of Pathology, 1987, pp. 358-372, vol. 127, Issue 2.

PMcL Black et al., "Immunological, biological, ultrastructural, and electrophysiological characteristics of a human glioblastoma-derived cell culture line," J. Neurosurg., 1982, pp. 62-72, vol. 56.

PL Kornblith, "The role of cytotoxic chemotherapy in the treatment of malignant brain tumors," Surg Neurol, 1995, pp. 551-552, vol. 44.

WC Welch et al., "Morphologic immunologic, biochemical and cytogenetic characteristics of the human glioblastoma-derived cell line, SNB-19," Journal of the Society for In Vitro Biology, 1995, pp. 610-616, vol. 31.

E Sariban et al., "DNA crosslinking responses of human malignant glioma cell strains to chloroethylnitrosoureas, cisplatin and diaziquone," Cancer Research, 1987, pp. 3988-3994, vol. 47, Issue 15.

* cited by examiner

METHOD FOR SELECTING THERAPEUTIC AGENTS FOR CANCER TREATMENT

RELATED APPLICATION

This application is a Continuation of application Ser. No. 11/504,098, filed Aug. 15, 2006 now U.S. Pat. No. 7,563,593, which is a Continuation of application Ser. No. 11/073,931, filed Mar. 8, 2005, now U.S. Pat. No. 7,112,415, which is a Continuation of U.S. application Ser. No. 09/039,957, filed Mar. 16, 1998, now U.S. Pat. No. 6,933,129, which is a Continuation-In-Part of U.S. application Ser. No. 08/679,056, filed Jul. 12, 1996, now U.S. Pat. No. 5,728,541, each of which is hereby incorporated by reference in its entirety.

FIELD OF THE INVENTION

The invention relates to screening and testing of active agents, including chemotherapeutic agents, to predict potential efficacy in individual patients in whom treatment with such agents is indicated. The invention also relates to a method for screening for expression of cellular markers, secreted factors or tumor antigens by cells for determining the disease state of the cells and for monitoring the potential efficacy of treatment agents.

INTRODUCTION

All active agents including chemotherapeutic active agents are subjected to rigorous testing as to efficacy and safety prior to approval for medical use in the United States. Methods of assessing efficacy have included elaborate investigations of large populations in double blind studies as to a given treatment method and/or active agent, with concomitant statistical interpretation of the resulting data, but these conclusions are inevitably generalized as to patient populations taken as a whole. In many pharmaceutical disciplines and particularly in the area of chemotherapy, however, the results of individual patient therapy may not comport with generalized data—to the detriment of the individual patient. The need has been long recognized for a method of assessing the therapeutic potential of active agents, including but not limited to chemotherapeutic agents, for their efficacy as to a given individual patient, prior to the treatment of that patient.

Prior art assays already exist which expose malignant tissue of various types to a plurality of active agents, for the purpose of assessing the best choice for therapeutic administration. For example, in Kruczynski, A., et al., "Evidence of a direct relationship between the increase in the in vitro passage number of human non-small-cell-lung cancer primocultures and their chemosensitivity," *Anticancer Research*, vol. 13, no. 2, pp. 507-513 (1993), chemosensitivity of non-small-cell-lung cancers was investigated in in vivo grafts, in in vitro primocultures and in commercially available long-term cancer cell lines. The increase in chemosensitivity was documented and correlated with morphological changes in the cells in question. Sometimes animal model malignant cells and/or established cell cultures are tested with prospective therapy agents, see for example Arnold, J. T., "Evaluation of chemopreventive agents in different mechanistic classes using a rat tracheal epithelial cell culture transformation assay," *Cancer Res*., vol. 55, no. 3, pp. 537-543 (1995).

In vitro prior art techniques present the further shortcoming that assayed cells do not necessarily express the cellular markers they would express in vivo. This is regrettable because the determination of expression of certain secreted or cellular markers, secreted factors or tumor antigens or lack thereof can be useful for both identification and therapeutic purposes. For instance, members of the fibrinolytic system such as urokinase-type plasminogen activator (u-PA) and plasminogen activator inhibitors type 1 (PAI-1) are up-regulated in malignant brain tumors. See, e.g., Jasti S. Rao, et al., "The Fibrinolytic System in Human Brain Tumors: Association with Pathophysiological Conditions of Malignant Brain Tumors," Advances in Neuro-Oncology II, Kornblith P L, Walker M D (eds) Futura 1997. Other secreted factors such as α-fetoprotein, carcinoembryonic antigen and transforming growth factors α and β have been found to be indicative of various cancers and/or cancer progression (see also, Singhal et al., "Elevated Plasma Osteopontin in Metastatic Breast Cancer Associated with Increased Tumor Burden and Decreased Survival," Clinical Cancer Research, Vol. 3, 605-611, April 1997; Kohno et al., "Comparative Studies of CAM 123-6 and Carcinoembryonic Antigen for the Serological Detection of Pulmonary Adenocarcinoma," Cancer Detection and Prevention, 21(2): 124-128 (1997)). These examples are but a few of the many factors that may be used to identify diseased cells.

Often the diseased cells express a cellular marker that is indicative of a certain disease state or lack thereof. However, one aspect of the culture techniques of the present invention is that the cultured diseased cells do not necessarily have to be the cells expressing the factor to be assayed. One question that inevitably arises when considering whether a serum marker is indicative of a particular cancer cell is, which cells produce the marker, the cell or the tissue in which the cancer cells grow? See e.g. Singhal et al., p 610. By co-culturing the cancerous tissue within a multicellular particulate of its originating tissue, the cells (both the diseased cells or the surrounding cells) are better able to retain their production of characteristic markers.

When actual patient cells are used to form in vitro assays focused on individual patients, in typical prior art processes the cells are harvested (biopsied) and trypsinized (connective tissue digested with the enzyme trypsin) to yield a cell suspension suitable for conversion to the desired tissue culture form. The in vitro tissue culture cell collections which result from these techniques are generally plagued by their inability accurately to imitate the chemosensitivity of the original tumor or other cell biopsy. These collections often do not express cellular markers in the same manner that they would in vivo. Standard cloning and tissue culture techniques are moreover excessively complicated and expensive for use in a patient-by-patient assay setting. A need thus remains for a technique of tissue culture preparation which provides cell cultures, for drug screening purposes, in which after simple preparation the cell cultures react in a manner equivalent to their in vivo reactivity, to enable drug or chemotherapeutic agent screening as to a particular patient for whom such screening is indicated. A need also remains for a technique of tissue culture preparation which provides cell cultures for screening for expressed markers or factors where the cultured cells express the markers or factors in a manner indicative of their in vivo expression of the same.

SUMMARY OF THE INVENTION

In order to meet these needs, the present invention is an improved system for screening a multiple of candidate therapeutic or chemotherapeutic agents for efficacy as to a specific patient, in which a tissue sample from the patient is harvested, cultured and separately exposed to a plurality of treatments and/or therapeutic agents for the purpose of objectively identifying the best treatment for the cultured cells obtained from the patient. The culture techniques of the present invention also result in a monolayer of cells that express cellular markers, secreted factors and tumor antigens in a manner representative of their expression in vivo. Specific method innovations such as tissue sample preparation techniques render this method practically as well as theoretically useful. One particularly important tissue sample preparation technique is the initial preparation of cohesive multicellular particulates of the tissue sample, rather than enzymatically dissociated cell suspensions or preparations, for initial tissue culture monolayer preparation. With respect to the culturing of malignant cells, for example, it is believed (without any intention of being bound by the theory) that by maintaining the malignant cells within a multicellular particulate of the originating tissue, growth of the malignant cells themselves is facilitated versus the overgrowth of fibroblasts or other cells which tends to occur when suspended tumor cells are grown in culture. Practical monolayers of cells may thus be formed to enable meaningful screening of a plurality of treatments and/or agents as well as meaningful identification of cellular markers. In the drug assays, growth of cells is monitored to ascertain the time to initiate the assay and to determine the growth rate of the cultured cells; sequence and timing of drug addition is also monitored and optimized. By subjecting uniform samples of cells to a wide variety of active agents (and concentrations thereof), the most efficacious agent can be determined. For assays concerning cancer treatment, a two-stage evaluation is contemplated in which both acute cytotoxic and longer term inhibitory effects of a given anti-cancer agent are investigated.

With regard to the identification of expressed cellular markers, secreted factors or tumor antigens, with the initial culturing of the multicellular particulates it is believed (without any intention of being bound by the theory) that because the cells are grown under conditions closer to those found in vivo, the cells express their cellular markers, secreted factors and tumor antigens in a manner more closely resembling their expression in vivo. By assaying the culture media obtained from growing a monolayer according to the inventive method or by histochemically and/or immunohistochemically assaying the cells grown under such conditions, a more accurate profile of the cellular markers or factors is obtained.

DETAILED DESCRIPTION OF THE INVENTION

The present invention is a system for screening a multiple of candidate therapeutic or chemotherapeutic agents for efficacy as to a specific patient, in which a tissue sample from the patient is harvested and separately exposed to a plurality of treatments and/or therapeutic agents for the purpose of objectively identifying the best treatment or agent. Specific method innovations such as tissue sample preparation techniques render this method practically as well as theoretically useful. One particularly important tissue sample preparation technique is the initial preparation of cohesive multicellular particulates (explants) of the tissue sample, rather than enzymatically dissociated cell suspensions or preparations, for initial tissue culture monolayer preparation. Cell growth, and sequence and timing of drug addition, are monitored and optimized.

An important application of the present invention is the screening of chemotherapeutic agents and other antineoplastic therapies against tissue culture preparations of malignant cells from the patients from whom malignant samples are biopsied. Related anti-cancer therapies which can be screened using the inventive system are both radiation therapy and agents which enhance the cytotoxicity of radiation, as well as immunotherapeutic anti-cancer agents. Screening processes for treatments or therapeutic agents for nonmalignant syndromes are also embraced within this invention, however, and include without limitation agents which combat hyper proliferative syndromes, such as psoriasis, or wound healing agents. Nor is the present efficacy assay limited only to the screening of active agents which speed up (healing) or slow down (anti-cancer, anti-hyper proliferative) cell growth because agents intended to enhance or to subdue intracellular biochemical functions may be tested in the present tissue culture system also. For example, the formation or blocking of enzymes, neurotransmitters and other biochemicals may be screened with the present assay methods prior to treatment of the patient.

When the patient is to be treated for the presence of tumor, in the preferred embodiment of the present invention a tumor biopsy of >100 mg of non-necrotic, non-contaminated tissue is harvested from the patient by any suitable biopsy or surgical procedure known in the art. Biopsy sample preparation generally proceeds as follows under a Laminar Flow Hood which should be turned on at least 20 minutes before use. Reagent grade ethanol is used to wipe down the surface of the hood prior to beginning the sample preparation. The tumor is then removed, under sterile conditions, from the shipping container and is minced with sterile scissors. If the specimen arrives already minced, the individual tumor pieces should be divided into four groups. Using sterile forceps, each undivided tissue quarter is then placed in 3 ml sterile growth medium (Standard F-10 medium containing 17% calf serum and a standard amount of Penicillin and Streptomycin) and systematically minced by using two sterile scalpels in a scissor-like motion, or mechanically equivalent manual or automated opposing incisor blades. This cross-cutting motion is important because the technique creates smooth cut edges on the resulting tumor multicellular particulates. Preferably but not necessarily, the tumor particulates each measure 1 $mm^3$. After each tumor quarter has been minced, the particles are plated in culture flasks using sterile pasteur pipettes (9 explants per to-25 or 20 particulates per to-75 flask). Each flask is then labeled with the patient's code, the date of explanation and any other distinguishing data. The explants should be evenly distributed across the bottom surface of the flask, with initial inverted incubation in a 37° C. incubator for 5-10 minutes, followed by addition of about 5-10 ml sterile growth medium and further incubation in the normal, non-inverted position. Flasks are placed in a 35° C., non-$CO_2$ incubator. Flasks should be checked daily for growth and contamination. Over a period of a few weeks, with weekly removal and replacement of 5 ml of growth medium, the explants will foster growth of cells into a monolayer. With respect to the culturing of malignant cells, it is believed (without any intention of being bound by the theory) that by maintaining the malignant cells within a multicellular particulate of the originating tissue, growth of the malignant cells themselves is facilitated versus the overgrowth of fibroblasts (or other unwanted cells) which tends to occur when suspended tumor cells are grown in culture.

The use of the above procedure to form a cell monolayer culture maximizes the growth of malignant cells from the tissue sample, and thus optimizes ensuing tissue culture assay of chemotherapeutic action of various agents to be tested. Enhanced growth of actual malignant cells is only one aspect of the present invention, however; another important feature is the growth rate monitoring system used to oversee growth of the monolayer once formed. Once a primary culture and its derived secondary monolayer tissue culture has been initiated, the growth of the cells is monitored to ascertain the time to initiate the chemotherapy assay and to determine the growth rate of the cultured cells.

Monitoring of the growth of cells is conducted by counting the cells in the monolayer on a periodic basis, without killing or staining the cells and without removing any cells from the culture flask. The counting may be done visually or by automated methods, either with or without the use of estimating techniques known in the art (counting in a representative area of a grid multiplied by number of grid areas, for example). Data from periodic counting is then used to determine growth rates which may or may not be considered parallel to growth rates of the same cells in vivo in the patient. If growth rate cycles can be documented, for example, then dosing of certain active agents can be customized for the patient. The same growth rate can be used to evaluate radiation treatment periodicity, as well. It should be noted that with the growth rate determinations conducted while the monolayers grow in their flasks, the present method requires no hemocytometry, flow cytometry or use of microscope slides and staining, with all their concomitant labor and cost.

Protocols for monolayer growth rate generally use a phase-contrast inverted microscope to examine culture flasks incubated in a 37° C. (5% $CO_2$) incubator. When the flask is placed under the phase-contrast inverted microscope, ten fields (areas on a grid inherent to the flask) are examined using the 10× objective, with the proviso that the ten fields should be non-contiguous, or significantly removed from one another, so that the ten fields are a representative sampling of the whole flask. Percentage cell occupancy for each field examined is noted, and averaging of these percentages then provides an estimate of overall percent confluency in the cell culture. When patient samples have been divided between two or among three or more flasks, an average cell count for the total patient sample should be calculated. The calculated average percent confluency should be entered into a process log to enable compilation of data—and plotting of growth curves—over time. Monolayer cultures may be photographed to document cell morphology and culture growth patterns. The applicable formula is:

$$\text{Percent confluency} = \frac{\text{estimate of the area occupied by cells}}{\text{total area in an observed field.}}$$

As an example, therefore, if the estimate of area occupied by the cells is 30% and the total area of the field is 100%, percent confluency is 30/100, or 30.

Adaptation of the above protocol for non-tumor cells is straightforward and generally constitutes an equivalent procedure.

Active agent screening using the cultured cells does not proceed in the initial incubation flask, but generally proceeds using plates such as microtiter plates. The performance of the chemosensitivity assay used for screening purposes depends on the ability to deliver a reproducible cell number to each row in a plate and/or a series of plates, as well as the ability to achieve an even distribution of cells throughout a given well. The following procedure assures that cells are reproducibly transferred from flask to microtiter plates, and cells are evenly distributed across the surface of each well.

The first step in preparing the microtiter plates is, of course, preparing and monitoring the monolayer as described above. The following protocol is exemplary and susceptible of variation as will be apparent to one skilled in the art. Cells are removed from the culture flask and a cell pellet is prepared by centrifugation. The cell pellet derived from the monolayer is then suspended in 5 ml of the growth medium and mixed in a conical tube with a vortex for 6 to 10 seconds. The tube is then rocked back and forth 10 times. A 36 μl droplet from the center of the conical tube is pipetted onto one well of a 96 well plate. A fresh pipette is then used to pipette a 36 μl aliquot of trypan blue solution, which is added to the same well, and the two droplets are mixed with repeated pipette aspiration. The resulting admixture is then divided between two hemocytometer chambers for examination using a standard light microscope. Cells are counted in two out of four hemocytometer quadrants, under 10× magnification. Only those cells which have not taken up the trypan blue dye are counted. This process is repeated for the second counting chamber. An average cell count per chamber is thus determined. Using means known in the art, the quadrant count values are checked, logged, multiplied by $10^4$ to give cells/ml, and the total amount of fluid (growth medium) necessary to suspend remaining cell aliquots is calculated accordingly.

After the desired concentration of cells in medium has been determined, additional cell aliquots from the monolayer are suspended in growth medium via vortex and rocking and loaded into a Terasaki dispenser known in the art. Aliquots of the prepared cell suspension are delivered into the microtiter plates using Terasaki dispenser techniques known in the art. A plurality of plates may be prepared from a single cell suspension as needed. Plates are then wrapped in sterile wet cotton gauze and incubated in an incubator box by means known in the art.

After the microtiter plates have been prepared, exposure of the cells therein to active agent is conducted according to the following exemplary protocol. During this portion of the inventive assay, the appropriate amount of specific active agent is transferred into the microtiter plates prepared as described above. A general protocol, which may be adapted, follows. Each microtiter plate is unwrapped from its wet cotton gauze sponge and microscopically examined for cell adhesion. Control solution is dispensed into delineated rows of wells within the grid in the microtiter plate, and appropriate aliquots of active agent to be tested are added to the remaining wells in the remaining rows. Ordinarily, sequentially increasing concentrations of the active agent being tested are administered into progressively higher numbered rows in the plate. The plates are then rewrapped in their gauze and incubated in an incubator box at 37° C. under 5% $CO_2$. After a predefined exposure time, the plates are unwrapped, blotted with sterile gauze to remove the agent, washed with Hank's Balance Salt Solution, flooded with growth medium, and replaced in the incubator in an incubator box for a predefined time period, after which the plates may be fixed and stained for evaluation.

Fixing and staining may be conducted according to a number of suitable procedures; the following is representative. After removal of the plates from the incubator box, culture medium is poured off and the plates are flooded with Hank's Balance Salt Solution. After repeated flooding (with agitation each time) the plates are then flooded with reagent grade ethanol for 2-5 minutes. The ethanol is then poured off. Staining is accomplished with approximately 5 ml of Giemsa Stain per plate, although volume is not critical and flooding is the goal. Giemsa stain should be left in place 5 min.±30 seconds as timing influences staining intensity. The Giemsa stain is then poured off and the plates are dipped three times in cold tap water in a beaker. The plates are then inverted, shaken vigorously, and air dried overnight (with plate lids off) on a rack on a laboratory bench. Cells per well are then counted manually or by automated and/or computerized means, to derive data regarding chemosensitivity of cells at various concentrations of exposure. One particularly useful computer operating environment for counting cells is the commercially available OPTIMATE compiler, which is designed to permit an optical counting function well suited to computerized cell counting procedures and subsequent calculations.

The above procedures do not change appreciably when cell growth promoters are assayed rather than cell arresting agents such as chemotherapeutic agents. The present assay allows cell death or cell growth to be monitored with equal ease. In any case, optimization of use of the present system will involve the comparative testing of a variety of candidate active agents for selection of the best candidate for patient treatment based upon the in vitro results. One particularly advantageous embodiment of the above described invention comprises a two-stage assay for cytotoxicity followed by evaluation of longer-term inhibitory effect. Chemotherapeutic agents may thus be evaluated separately for both their direct chemotherapeutic effect as well as for their longer duration efficacy.

Identification of one or more active agents or chemotherapeutic agents is peripheral to the present invention, which is intended for the efficacy screening of any or all of them as to a given patient. Literally any active agent may be screened according to the present invention; listing exemplary active agents is thus omitted here.

The essence of the invention thus includes the important feature of the simplicity of the present system—cohesive multicellular particulates of the patient tissue to be tested are used to form cell monolayers; growth of those monolayers is monitored for accurate prediction of correlating growth of the same cells in vivo; and differing concentrations of a number of active agents may be tested for the purpose of determining not only the most appropriate agent but the most appropriate concentration of that agent for actual patient exposure (according to the calculated cell growth rates). It is also important to note, in the context of the invention, that the present system allows in vitro tests to be conducted in suspensions of tissue culture monolayers grown in nutrient medium under fast conditions (a matter of weeks), rather than with single cell progeny produced by dilution cloning over long periods of time. In some cases, the present invention is a two stage assay for both cytotoxicity and the longer-term growth inhibitory.

Another important aspect of the present invention is to provide a system for screening specific tissue samples from individual patients for expressed cellular markers, secreted factors or antigens, including tumor antigens, characteristic of the tissue sample. A tissue sample from a patient is harvested and grown in a monolayer culture as described above. Culture medium in which the primary monolayer culture or subcultures thereof can then be assayed for the presence or absence of certain factors, such as secreted tumor antigens like PAI-1, u-PA or carcinoembryonic antigen. These factors may be detected through use of standard assays such as radioimmunoassay (RIA) or enzyme-linked immunosorbent assay (ELISA) although the many other assays known to those skilled in the art may be used to detect and/or quantify the soluble factors. The cell cultures grown in this manner may also be assayed histochemically and or immunohistochemically for identification or quantification of cellular or membrane-bound markers. By screening tissue samples in this manner for production of such factors, markers or antigens, the cultured cells may be further identified, aiding the physician in treatment strategies and as a prognosis indicator. Furthermore, by combining the use of the culture technique with assaying for such markers, factors and antigens, a treatment strategy for a disease state may be optimized and treatment progression may be monitored.

Lastly, immunological markers may be monitored in applications requiring up- or down- regulation of such markers (i.e., Major histocompatibility complex molecules). This aspect of the present invention can be especially useful in transplantation applications where, for instance, through chemical or biological means rejection of transplanted cells is sought to be avoided by down-regulation of the various transplantation antigens present on the cells to be transplanted. The present invention would be especially useful in monitoring such immunoregulation.

EXAMPLE 1

Radiation Therapy

Separate 50 mg samples from residual tissue from specimens of three human glioblastomas and one human ovarian carcinoma were minced in medium with sterile scissors to a particle size of roughly 1 $mm^3$ and with a particle size distribution between about 0.25 and about 1.5 mm3. The medium was Standard F-10 medium containing 17% calf serum and a standard amount of Penicillin and Streptomycin. Each 50 mg sample was minced and was divided into four groups of particulates and each of 16 groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the 16 flasks. Each cell pellet was then suspended in 5 ml of the above-described medium and was mixed in a conical tube with a vortex for 6 to 10 seconds, followed by manual rocking back and forth 10 times. A 36 microliter droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 16 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours later, the cells were irradiated using a Siemens Stabilipan X-ray machine at 250 kVp, 15 mA with a dose rate of 75 rad/minute. For each radiation dose from 1 Gy to 6 Gy, cell number per well was monitored as a function of time through five days post-irradiation.

Cell number relative to controls was determined and survival curves were fit to the data. The rate of decrease in survival as a function of time was proportional to dose. A differential radiation response among the four cell lines was observed.

EXAMPLE 2

Immuno Therapy

Separate 50 mg samples from residual tissue from specimens of a human brain tumor, renal carcinoma, and breast carcinoma were minced in medium with sterile scissors to a particle size of roughly 1 $mm^3$ and with a particle size distribution between about 0.25 and about 1.5 $mm^3$. The medium was Standard F-10 medium containing 17% calf serum and a standard amount of Penicillin and Streptomycin. Each 50 mg sample was minced and was divided into four groups of particulates and each of 12 groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the twelve flasks. Each cell pellet was then suspended in 5 ml of the above-described medium and was mixed in a conical tube with a vortex for 6 to 10 seconds, followed by manual rocking back and forth 10 times. A 36 microliter droplet from the center of each tube was then pipetted into one well a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 12 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating, Activated Natural Killer (ANK) cells were delivered into a row of six wells by means of a micropipette. In each microtiter plate three rows of six wells each served as controls. The effector (ANK cells): target cell (tumor cells) ratio varied from 2.5:1 to 20:1. The ANK cells were exposed to the target cells for four hours. Subsequently, the wells were washed with Hanks Balanced Salt Solution and the number of ANK cells remaining in the wells was observed with a phase contrast microscope. This process was repeated until no ANK cells remained in the wells (usually 3 washes). Following removal of the ANK cells, the tumor cells were incubated in the wells for another 24 hours.

Cell number relative to control was determined. For the three tumor types increasing the effector:target cell ratio from 2.5:1 to 20:1 resulted in an increase in the number of tumor cells killed by the ANK cells.

EXAMPLE 3

Gene Therapy/Antisense Oligonucleotides

A 50 mg sample from a residual human mesothelioma was minced in medium with sterile scissors to a particle size of roughly 1 $mm^3$ and with a particle size distribution between about 0.25 and about 1.5 $mm^3$. The medium was Standard F-10 medium containing 17% calf serum and a standard amount of Penicillin and Streptomycin. The 50 mg sample was minced and was divided into four groups of particulates and each of four groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the four flasks. Each cell pellet was then suspended in 5 ml of the above-described medium and was mixed in a conical tube with a vortex for 6 to 10 seconds, followed by manual rocking back and forth 10 times. A 36 microliter droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the four monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating, antisense oligonucleotide for the urokinase-type plasminogen activator receptor (uPAR) was delivered to wells in the microtiter plate. Proteolysis of plasminogen to plasmin by urokinase-type plasminogen activator has been implicated in the processes of tumor cell proliferation and invasion. The concentrations of the uPAR antisense oligonucleotide were 1, 10 and 100 micromolar. uPAR sense and missense oligonucleotides at the concentrations of 1, 10 and 100 micromolar served as controls. The tumor cells were exposed to the oligonucleotides for 24 hours and then the agents were removed. The cells were allowed to incubate for another 72 hours so that inhibition of cell proliferation could be observed.

Cell number relative to control was then determined. Antisense oligonucleotides to uPAR suppressed the proliferative activity of the tumor cells in a concentration dependent manner.

EXAMPLE 4

Combination Chemotherapy

Separate 50 mg samples from residual tissue from specimens from four human ovarian tumors were minced in medium with sterile scissors to a particle size of roughly 1 $mm^3$ and with a particle size distribution between about 0.25 and about 1.5 $mm^3$. The medium was Standard F-10 medium containing 17% calf serum and a standard amount of Penicillin and Streptomycin. Each 50 mg sample was minced and was divided into four groups of particulates and each of 16 groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the 16 flasks. Each cell pellet was then suspended in 5 ml of the above-described medium and was mixed in a conical tube with a vortex for 6 to 10 seconds, followed by manual rocking back and forth 10 times. A 36 microliter droplet from the center of each tube was then pipetted into one well a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 16 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating, the chemotherapeutic agent taxol was applied to the wells in the microtiter plates. The first three treatment rows in the plates (Rows 2, 3, and 4) were designed to have escalating taxol doses (1.0, 5.0, and 25 μM) with a fixed carboplatin dose (200 μM). The last three treatment rows in the plates (Rows 6, 7, and 9) were designed to have a fixed taxol dose (5 μM) with an escalating carboplatin dose (50, 200, and 1000 μM). Rows 5 and 9 served as a control. The taxol exposure time was two hours. Twenty-four hours later, the cells in the wells were exposed to carboplatin for two hours. The tumor cells in the wells were then incubated for another 48 hours.

Cell number relative to control was determined. For the cells from the four tumor specimens a dose response relationship was observed for both the escalating taxol/fixed carboplatin and fixed taxol/escalating carboplatin treatment schema.

EXAMPLE 5

Hormonal Therapy

Separate 50 mg samples from residual tissue from specimens from four human breast tumors were minced in medium with sterile scissors to a particle size of roughly 1 $mm^3$ and with a particle size distribution between about 0.25 and about 1.5 $mm^3$. The medium was Standard F-10 medium containing 17% calf serum and a standard amount of Penicillin and Streptomycin. Each 50 mg sample was minced and was divided into four groups of particulates and each of 16 groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the 16 flasks. Each cell pellet was then suspended in 5 ml of the above-described medium and was mixed in a conical tube with a vortex for 6 to 10 seconds, followed by manual rocking back and forth 10 times. A 36 microliter droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 16 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating, the antiestrogenic compound tamoxifen was delivered to wells in the microtiter plates. A stock solution of tamoxifen was initially prepared by dissolving 1.5 mg of tamoxifen powder in 1 ml of absolute ethanol and then adding 9 ml of growth medium. This stock solution was then used to make tamoxifen solutions in the concentration range of 10 nM to 20 μM. Six doses of tamoxifen were used for cells from each of the four breast tumor specimens. An ethanol solution at a concentration equivalent to that at the highest tamoxifen concentration served as a control. The tumor cells were exposed to tamoxifen for 24 hours and then the agent was removed. The cells were allowed to incubate for another 72 hours so that inhibition of cell proliferation could be observed.

Cell number relative to control was then determined. There was no effect observed when the ethanol-only control wells were compared to the growth medium-only control wells.

The cells of two of the four breast specimens tested showed an inhibition of cell proliferation by tamoxifen exposure. These responses occurred in the mid to high tamoxifen concentration ranges.

EXAMPLE 6

Differentiating Agent Therapy ("Biological Response Modification")

Separate 50 mg samples from residual tissue from specimens from four human breast tumors were minced in medium with sterile scissors to a particle size of roughly 1 $mm^3$ and with a particle size distribution between about 0.25 and about 1.5 $mm^3$. The medium was Standard F-10 medium containing 17% calf serum and a standard amount of Penicillin and Streptomycin. Each 50 mg sample was minced and was divided into four groups of particulates and each of 16 groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the 16 flasks. Each cell pellet was then suspended in 5 ml of the above-described medium and was mixed in a conical tube with a vortex for 6 to 10 seconds, followed by manual rocking back and forth 10 times. A 36 microliter droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 16 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating the differentiating agent retinoic acid was delivered to wells in the microtiter plates. A stock solution of retinoic acid was initially prepared by dissolving retinoic acid powder in 1 ml of dimethyl sulfoxide (DMSO) and then adding 9 ml of growth medium. This stock solution was then used to make retinoic acid solutions in the concentration range of 0.1 to 1.0 mM. Six doses of retinoic acid were used for cells from each of the four breast tumor specimens. A DMSO solution at a concentration equivalent to that at the highest retinoic acid concentration served as a control. The tumor cells were exposed to retinoic acid for 24 hours and then the agent was removed. The cells were allowed to incubate for another 72 hours so that inhibition of cell proliferation could be observed.

Cell number relative to control was then determined. There was no effect observed when the DMSO-only control wells were compared to the growth medium-only control wells. The cells of three of the four breast specimens tested showed an inhibition of cell proliferation by retinoic acid exposure. These responses occurred in the mid to high retinoic acid concentration ranges.

EXAMPLE 7

Combined Modality Therapy Drug/Radiation

Separate 50 mg samples from residual tissue from specimens from two human brain tumors and two human ovarian tumors were minced in medium with sterile scissors to a particle size of roughly 1 $mm^3$ and with a particle size distribution between about 0.25 and about 1.5 $mm^3$. The medium was Standard F-10 medium containing 17% calf serum and a standard amount of Penicillin and Streptomycin. Each 50 mg sample was minced and was divided into four groups of particulates and each of 16 groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the 16 flasks. Each cell pellet was then suspended in 5 ml of the above-described medium and was mixed in a conical tube with a vortex for 6 to 10 seconds, followed by manual rocking back and forth 10 times. A 36 microliter droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 16 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating, cells in the microtiter plate wells were exposed to the chemotherapeutic agent taxol. One set of plates was designed to have escalating taxol doses with (0.5-25.0 μM) with a fixed radiation dose (2 Gy). A second set of plates was designed to have a fixed taxol dose (5 μM) with an escalating radiation dose (1 Gy-6 Gy). The cells in the plates were irradiated using a Siemans Stabilipan X-ray machine operating at 250 kVp, 15 mA with a dose rate of 75 rad/minute.

For each of the two treatment schema, cell number per well was monitored as a function of time through 5 days post-treatment. Cell number relative to controls was determined and survival curves were fit. A differential response among the cells from the four tumor specimens was observed. Both additive and synergistic cell killing was noted.

Although the present invention has been described with respect to specific materials and methods above, the invention is only to be considered limited insofar as is set forth in the accompanying claims.

I claim:

1. A method for determining the efficacy of a candidate chemotherapy for a patient prior to treatment, comprising the steps of:

separating a cancer patient's tissue specimen into multicellular particulates, wherein the patient's tissue specimen comprises tumor tissue and the multicellular particulates are not dissociated cell suspensions, wherein the tumor tissue is an ovarian carcinoma tumor, a breast carcinoma tumor, a renal carcinoma tumor, or a mesothelioma;

allowing said cohesive multicellular particulates to form one or more tissue culture monolayer(s) comprising growing malignant cells without overgrowth of fibroblasts;

suspending cells of the monolayer(s) in a plurality of segregated sites; and screening the cells in the segregated sites for sensitivity to a plurality of candidate chemotherapies indicated for treatment of said cancer, thereby determining the efficacy of each candidate chemotherapy for the patient prior to treatment.

2. The method of claim 1, wherein the specimen is from a tumor biopsy.

3. The method of claim 1, wherein the specimen is an ovarian carcinoma specimen.

4. The method of claim 1, wherein the specimen is a breast carcinoma specimen.

5. The method of claim 1, wherein the specimen is a renal carcinoma specimen.

6. The method of claim 1, wherein the specimen is a mesothelioma specimen.

7. The method of claim 2, wherein the tumor biopsy comprises at least 100 mg of non-necrotic tissue.

8. The method of claim 1, wherein the specimen is a sample of about 50 mg.

9. The method of claim 1, wherein the multicellular particulates have smooth cut edges.

10. The method of claim 9, wherein said smooth cut edges are created by systematic mincing in a scissor-like motion.

11. The method of claim 10, wherein the scissor-like motion is generated with manual or automated opposing incisor blades.

12. The method of claim 11, wherein the opposing incisor blades are scalpels.

13. The method of claim 1, wherein the multicellular particulates have a particle size distribution between about 0.25 and about 1.5 $mm^3$.

14. The method of claim 1, wherein the multicellular particulates have a size of about 1 $mm^3$.

15. The method of claim 1, wherein the multicellular particulates are not enzymatically dissociated cell suspensions.

16. The method of claim 1, wherein the multicellular particulates are plated in culture flasks for monolayer growth.

17. The method of claim 16, wherein less than about 20 multicellular particulates are plated per culture flask.

18. The method of claim 1, wherein the tissue culture monolayer(s) are formed in sterile growth medium, at about 35° C. in the absence of $CO_2$, and in a non-inverted position.

19. The method of claim 18, wherein the sterile growth medium comprises calf serum and antibiotic.

20. The method of 1, wherein the monolayer(s) are produced over a period of about 3 weeks.

21. The method of claim 20, wherein the monolayer(s) are checked approximately daily for growth and contamination.

22. The method of claim 20, further comprising, screening or monitoring the culture medium for production of one or more cellular markers, secreted factors, or tumor antigens that are indicative of the presence or absence of a disease state.

23. The method of claim 22, wherein the tumor antigen is PAI-1, u-PA, or carcinoembryonic antigen.

24. The method of claim 22, wherein the production of secreted factors is determined by ELISA or RIA.

25. The method of claim 20, further comprising, histochemically or immunohistochemically assaying cells of a monolayer.

26. The method of claim 20, wherein the sterile growth medium is replaced approximately weekly.

27. The method of claim 1, further comprising, monitoring the growth rate of the monolayer(s) to determine the time to initiate the chemosensitivity testing.

28. The method of claim 27, wherein the growth rate is monitored by counting the cells of the monolayer(s) on a periodic basis.

29. The method of claim 28, wherein the cells are counted without killing or staining the cells and without removing cells from the monolayer(s).

30. The method of claim 29, wherein the cells are counted with a phase-contrast inverted microscope.

31. The method of claim 30, wherein the cells are counted in a representative area of a grid, and the number of cells in the representative area is multiplied by the number of grid areas.

32. The method of claim 1, wherein the tissue culture monolayer(s) are photographed to document cell morphology and culture growth patterns.

33. The method of claim 31, wherein percent confluency of the monolayer(s) are estimated.

34. The method of claim 27, wherein the growth rate is indicative of the growth rate of the tumor in vivo.

35. The method of claim 34, wherein the growth rate is used to estimate dosing of chemotherapeutic agents for in vitro testing.

36. The method of claim 1, wherein the cells of the monolayer(s) are suspended prior to monolayer confluency.

37. The method of claim 36, wherein chemosensitivity testing is initiated with growing cells.

38. The method of claim 17, wherein the cells are suspended by:

removing the monolayer cells from the culture flask, preparing a cell pellet by centrifugation, suspending the cell pellet in about 5 ml of growth medium, counting the cells to determine the total amount of growth medium necessary to suspend the cells for chemosensitivity testing, and suspending the cells in the total amount of growth medium.

39. The method of claim 38, wherein the cells are counted with trypan blue.

40. The method of claim 1, wherein the segregated sites are wells of one or more microtiter plate(s).

41. The method of claim 40, wherein a reproducible number of suspended cells are delivered to each row in a plate or series of plates.

42. The method of claim 41, wherein about 100 cells are delivered per well.

43. The method of claim 42, wherein cells are evenly distributed across the surface of each well.

44. The method of claim 41, wherein the reproducible number of cells is delivered using a dispenser.

45. The method of claim 41, wherein the microtiter plates containing the suspended cells are incubated for about 24 hours prior to drug exposure.

46. The method of claim 45, wherein control solution, and a plurality of candidate chemotherapies, each at varying concentrations, are administered to the wells containing the cells.

47. The method of claim 46, wherein the plates containing the cells with a plurality of chemotherapies are incubated at 37° C. under 5% $CO_2$ for a predetermined period of time.

48. The method of claim 47, wherein the predetermined time is about 2 hours, or about 24 hours.

49. The method of claim 46, wherein at least one candidate chemotherapy is a combination therapy.

50. The method of claim 49, wherein the combination chemotherapy is taxol and carboplatin.

51. The method of claim 50, wherein the taxol and carboplatin are incubated with the cells consecutively.

52. The method of claim 47, wherein the plates are incubated for a two-stage assay, a first stage to determine acute cytotoxicity, and a second stage to determine a longer term inhibitory effect.

53. The method of claim 52, wherein drug is removed prior to incubation for the second stage.

54. The method of claim 52, wherein the first stage is an incubation for about 24 hours and the second stage is an incubation for about 72 hours.

55. The method of claim 47, wherein the cells are fixed and stained after the predetermined period of time.

56. The method of claim 55, wherein the cells are stained with Giemsa.

57. The method of claim 55, wherein the number of cells per well are counted.

58. The method of claim 57, wherein the number of cells per well is used to determine the chemosensitivity of the cells to the plurality of chemotherapies.

59. The method of claim 58, further comprising, comparing the chemosensitivity of the cells with each of the plurality of chemotherapies.

* * * * *